(12) United States Patent
Fahey (10) Patent No.: US 6,521,818 B1
(45) Date of Patent: Feb. 18, 2003

(54) DEVELOPMENT OF NOVEL HIGHLY CHEMOPROTECTANT CRUCIFER GERMPLASM

(75) Inventor: Jed W. Fahey, Eldersburg, MD (US)

(73) Assignee: John Hopkins School of Medicine, Baltimore, MD (US)

( * ) Notice: Subject to any disclaimer, the term of this patent is extended or adjusted under 35 U.S.C. 154(b) by 0 days.

(21) Appl. No.: 09/348,874

(22) Filed: Jun. 30, 1999

Related U.S. Application Data
(60) Provisional application No. 60/091,471, filed on Jul. 1, 1998.

(51) Int. Cl.$^7$ .......................... C12N 15/01; A01H 5/00; A01H 1/06

(52) U.S. Cl. ....................... 800/306; 800/260; 800/265; 800/270; 800/276; 800/278; 800/279; 800/298; 800/301; 800/302

(58) Field of Search ................................. 800/260, 265, 800/270, 276, 278, 279, 298, 301, 302, 306

(56) References Cited

U.S. PATENT DOCUMENTS

| | | | |
|---|---|---|---|
| 5,625,130 A | 4/1997 | Grant et al. | 800/200 |
| 5,770,789 A | * 6/1998 | Mithcell-Olds et al. | 800/200 |

FOREIGN PATENT DOCUMENTS

| | | |
|---|---|---|
| EP | 0 647 406 A2 | 4/1995 |

OTHER PUBLICATIONS

Fahey et al. The role of crucifers in cancer chemoportection. Current Topics in Plant Physiology, vol. 15, pp. 87–93, 1995.*
Iqbal et al. Biosynthesis of glucosinolates by microspore derived embryoids and plantlets in vitro of Brassica napus L., Plant Science, vol. 112, pp. 107–115, 1995.*
Prochaska et al. Rapid detection of inducers of enzymes that protect against carcinogens, Proceedings of the National Academy of Science USA, vol. 89, pp. 2394–2398, 1992.*
Zhang et al. A major inducer of anticarcinogenc protective enzymes from broccoli: Isolation and elucidation of structure, Proceedings of the National Academy of Sciences USA, vol. 89, pp. 2399–2403, 1992.*
A. Giamoustaris et al., "The effect of modifying the glucosinolate content of leaves of oilseed rape (Brassica napus ssp. Oleifera) on its interaction with specialist and generalist pests." Ann. Appl. Biol. vol. 126, No. 2, pp. 347–363.
The Sproutletter, No. 25, Nov.–Dec. 1984.
"The Sproutletter" May–Jun. 1981, No. 4.
Roy Bruder, Ph.D., Discovering Natural Foods, (including pp. 203–209), Woodbridge Press, 1982.
Brian R. Clement, Hippocrates Health Program, (including pp. 7–11), Hipprocrates Publications, 1989.
Jethro Kloss, The Back to Eden Cookbook, pp. 61–61, Woodbridge Press, 1974.
Steven Meyerowitz, Sproutmann Kitchen Garden Cookbook, The Sprouthouse, Inc., pp. 178–179, 290, 1994.
Steve Meyerowitz Sprout It, One week from Seed to Salad, The Sprouthouse, Inc., (including pp. 84–85, 120–123, 204 pages), Jun. 1994.
Steve Meyerowitz, The Complete Guide to Sprouting, Sprouts The Miracle Food, Sproutman Publications, (including pp. 121–122), 204 pages, May 1998.
Esther Munroe, Sprouts to Grow and Eat, (including pp. 2–15), 22 pages, Dec. 1974.
Jean Hewitt, The New York Times New Natural Foods Cookbook:, Avon Books, pp. 200–203, 1982.
Martha H. Oliver, Add a Few Sprouts To Eat Better for Less Money, Pivot Original Health Books, (including pp. 52–53, 118–119), 126 pages, 1975.
James C. Schmidt, Horticulture Facts, "Growing Sprouts Indoors", (Rev. 4/81).
Angnes Toms, The Joy of Eating Natural Foods, The Complete Organic Cookbook, pp. 318–319, Nov. 1971.
Karen Cross Whyte, The Complete Sprouting Cookbook, Troubador Press, (including pp. 57–59), 120 pages, 1973.
Ann Wigmore, The Sprouting Book, Avery Publications, (including pp. 29–37), 116 pages, 1986.
Debra Schwarze, Growing Sprouts, Neb Guide, Jan. 1989.
John Tobe, Sprouts Elixir of Life, 112 pages, The Provoker Press, 1970.
David Ehrlich with George Wolf, Foreward by Peter Albright, M.D., "The Bowell Book", Schocken Books, 175 pages, 1981.
"The Good News Sprouts Recipe Book" ISGA, 112 pages, Aug. 1992.
Ann Wigmore, "The Hippocrates Diet and Health Program", Avery Publications, 191 pages, 1984.
Sprouting Publications Oahspe Foundation, Health and Sprouting Supplies.
Sproutletter, #41, Summer, 1989.

(List continued on next page.)

Primary Examiner—Elizabeth F. McElwain
Assistant Examiner—Medina A. Ibrahim
(74) Attorney, Agent, or Firm—Foley & Lardner (57) ABSTRACT

A method for producing crucifer germplasm, in particular broccoli and cauliflower germplasm, with high levels of cancer chemoprotectant agents is provided which comprises screening a population of plants for glucosinolate profiles and selecting an individual plant with an enhanced alkyl/indole glucosinolate ratio. Subsequent breeding with a selected plant results in varieties, lines, and plants with desirable glucosinolate profiles. A method of growing crucifer sprouts to enhance chemoprotectant activity of the sprouts by germinating the seeds in a limited water volume is also provided. A method for producing crucifer germplasm which produces seeds with reduced leakage of seed material is provided which comprises screening a population of plants for production of seeds with reduced leakage and selecting an individual plant which produces such seeds.

13 Claims, 2 Drawing Sheets

OTHER PUBLICATIONS

The Sproutletter, No. 27, Mar.–Apr. 1985.
Steve Meyerowitz, Growing Vegetables Indoors, 85 pages, The Sprout House, 1983.
The Sproutletter, No. 24, Sep.–Oct. 1984.
The Sproutletter, Issue 33, Spring 1987.
The Sproutletter, No. 28, May–Jun. 1985.
The Sproutletter, No. 26, Jan.–Feb. 1985.
Sprouting Publications, Health and Sprouting Supplies.
The Sproutletter, No. 29, Jul.–Aug. 1985.
Sproutletter, #40, Spring, 1989.
The Sproutletter, No. 32, Summer.
Sproutletter, #44, Mar. 1991.
Sproutletter, #36, Winter, 1987–1988.
Sproutletter, #39, Fall, 1988.
Sproutletter, #43, May/Jun. 1990.
Sproutletter, #38, Summer, 1988.
Sprouting Publications Health and Sprouting Supplies. Spring Sale for Members Only.
The Sproutletter, A newletter of useful and unusual information on sprouts, raw foods and nutrition.
The Sproutletter, #31, Winter.
Deirdre Purdy, ed., The Summer Kitchen, A Farmers' Market Cookbook, 96 pages, 1981.
Viktoras Kulvinskas, M.S. Co–Director Hippocrates Health Institute, "Love Your Body or how to be a live food lover", 95 pages, 1974.
The Sprout House Article from Newspaper.
New Prices—New Products, Jul. 1985 order form.
Steve Meyerowitz, Indoor Vegetable Kit, The Sprout House.
The Sprout House Newsletter, Issue #15, Aug., 1992.
Sproutman's Exotic Seeds for Sprouting 100% Organically Grown Order Form.
Complaint for Patent Infringement (Brassica Protection Products, LLC v. The Sproutman, Inc. dated Sep. 20, 1999.
Murry Tizer's Answer, Afirmative Defenses and Counterclaims dated Jun. 28, 1999.
The Sproutman, Inc.'s. Answer, Afirmative Defenses and Counterclaims dated Jun. 28, 1999.
Request fro Reexamination of U.S. Patent No. 5,725,895 filed Oct. 11, 1999.

* cited by examiner

DEVELOPMENT OF NOVEL HIGHLY CHEMOPROTECTANT CRUCIFER GERMPLASM

This application claims the benefit of U.S. Provisional Application No.60/091, 471, filed Jul. 1, 1998.

This invention was made with U.S. Government support under NIH grant 1PO1 CA44530, and the U.S. Government has certain rights in this invention.

BACKGROUND OF THE INVENTION

1. Field of the Invention

This invention relates to methods for developing novel, highly chemoprotectant crucifer germplasm. In particular, this invention relates to methods for developing novel, highly chemoprotectant broccoli and cauliflower germplasm. The invention relates to the development of germplasm which contains significant quantities of chemoprotective compounds that modulate mammalian enzymes which are involved in metabolism of carcinogens. These compounds induce the activity of Phase 2 enzymes, without inducing biologically significant activities of those Phase 1 enzymes that activate carcinogens. More specifically, the novel germplasm contains an enhanced alkyl/indole glucosinolate ratio.

This invention further provides a method of germinating cruciferous seeds and sprouts under conditions which increase antibiotic activity against a range of human pathogens, and which increase the chemoprotectant activity of the sprouts.

2. Description of the Related Art

It is widely recognized that diet plays a large role in controlling the risk of developing cancers and that increased consumption of fruits and vegetables reduces cancer incidence in humans. It is now believed that a major mechanism of protection depends on the presence of chemical components in plants that, when delivered to mammalian cells, elevate levels of Phase 2 enzymes that detoxify carcinogens.

Phase 2 enzymes are effective by detoxifying electrophilic forms of carcinogens which would otherwise damage DNA. Compounds which elevate the level of Phase 2 enzymes are termed "selective inducers." Selective inducers of Phase 2 enzymes are designated monofunctional inducers. This means that they induce only Phase 2 enzymes, without significantly inducing Phase 1 enzyme activities. In contrast, compounds which induce both Phase 2 and Phase 1 enzymes are designated bifunctional inducers. (see Prochaska & Talalay (1988) *Cancer Res.* 48: 4776–4782). The monofunctional inducers are nearly all electrophiles and belong to at least 9 distinct chemical classes. (see Prestera et al. (1993) *Proc. Natl. Acad. Sci. USA* 90: 2963–2969; Khachick et al. (1999) in ANTIOXIDANT FOOD SUPPLEMENTS IN HUMAN HEALTH, Packer, L. et al. (eds) pp 203–229, Academic Press, San Diego). The only apparent common property, shared by almost all of these inducers is their ability to react with thiol groups.

Monofunctional inducers are thus chemoprotective agents which reduce the susceptibility of mammals to the toxic and neoplastic effects of carcinogens. Chemoprotectors can be of plant origin or synthetic compounds. Synthetic analogs of naturally occurring inducers have also been generated and shown to block chemical carcinogenesis in animals. (see Posner et al. (1994) *J. Med. Chem.* 37: 170–176; Zhang et al. (1994) *Proc. Natl. Acad. Sci. USA* 91: 3147–3150; Zhang et al. (1994) *Cancer Res.* (Suppl) 54: 1976s–1981s).

Highly efficient methods have been developed for measuring the potency of plant extracts to increase or induce the activities of Phase 2 enzymes (Prochaska & Santamaria (1988) *Anal. Biochem.* 169: 328–336 and Prochaska et al. (1992) *Proc. Natl. Acad. Sci. USA* 89: 2394–2398). In addition, these methods have been employed for isolating the compounds responsible for the inducer activities in plants and for evaluating the anticarcinogenic activities of these compounds and their synthetic analogs (Zhang et al. (1992) *Proc. Natl. Acad. Sci. USA* 89: 2399–2403 and Posner et al. (1994) *J. Med. Chem.* 17: 170–176).

These methods have identified crucifer plants as a possible source of inducer activity. However, the levels of inducer activity among individual plants are highly variable, depending on the variety and on the growth and harvesting conditions.

It is now known that most of the inducer activity of crucifer plants is due to the presence and amounts of isothiocyanates and their biogenic precursors, glucosinolates. Glucosinolates are converted to isothiocyanates by the enzyme myrosinase, which is a thioglucoside glucohydrolase. Normally, myrosinase and glucosinolates are separated in the cell. If the cell is damaged, resulting in disruption of cellular compartmentalization, myrosinase comes into contact with glucosinolates, and converts them to isothiocyanates.

Although glucosinolates are not themselves inducers of mammalian Phase 2 enzymes, their conversion products, by virtue of myrosinase activity, are. Thus, it is the isothiocyanate products which are potent monofunctional inducers of Phase 2 enzymes in the murine hepatoma cell bioassay of QR activity.

However, not all glucosinolates produce isothiocyanates which are inducers of Phase 2 enzymes. Certain glucosinolates (e.g. alkylthioalkyl glucosinolates) produce isothiocyanates that are potent chemoprotective agents. Other glucosinolates (e.g. indole glucosinolates), produce compounds such as indole-3-carbinol and indole-3-acetonitrile, that are problematic for several reasons. First, such compounds are bifunctional inducers; that is, they induce both Phase 2 and Phase 1 enzymes. Phase 1 enzymes can activate xenobiotics thereby creating carcinogens. (Prochaska & Talalay (1988) *Cancer Res.* 48: 4776–4782). Second, the indole glucosinolates are only weak inducers of Phase 2 enzymes (Fahey J W et al. (1998) Chapter 2 in FUNCTIONAL FOODS FOR DISEASE PREVENTION I. Shibamoto T. et al. (eds), pp 16–22, ACS Symposium Series 701, Am Chem Soc, Washington D.C.). Third, these compounds themselves function as tumor promoters (Kim D J et al. (1997) *Carcinogenesis* 18(2):377–381). Finally, these compounds can form condensation products under the acid conditions encountered in the stomach, which are potent carcinogens very similar to dioxin (TCDD) (Bjeldanes L F et al. (1991) *Proc Nat Acad Sci USA* 88:9543–9547).

Thus, the amounts of inducer activity depends upon both the quality and quantity of glucosinolates present in crucifer plants. Market stage broccoli and cauliflower, for example, contain among the highest levels of the alkylthioalkyl glucosinolates, 4-methylsulfinylbutyl and 3-methylsulfinylpropyl glucosinolate, thus far identified in vegetables. They also contain, however, similar levels of the indole glucosinolates, glucobrassicin (indolyl-3-methyl glucosinolate), neoglucobrassicin, and 4-hydroxyglucobrassicin. Broccoli and cauliflower germinated seeds, sprouts, and young plantlets, on the other hand, contain higher concentrations of glucosinolates than do the market stage vegetable. The amount of glucosinolates present in the sprouts may depend to some extent upon the leakage of glucosinolates from the seeds upon imbibition and germination.

The processes of seed imbibition and germination, as well as priming, osmoconditioning, matri-conditioning and the like, though primarily associated with a net influx of water to the seed and seedling, also typically involve the leaking or leaching of chemicals from the germinating seed. The amount of chemicals leaking from the seed can be regulated by the milieu in which the seed is placed, although some leakage is inevitable. Furthermore, the amount of leakage may also be related to the quality of the seed lot, and to the type of seed.

The leachates of cruciferous seeds can exhibit potent antibiotic activity. This activity is effective not only against a range of human pathogens, but also against other microbes which commonly thrive or co-exist in commercial green sprout (such as bean sprout or green leafy sprout) production systems, which thus effectively contaminate these systems. The antibiotic activity of germinating crucifer seeds, in both the seeds and seedlings and the leachate resulting therefrom, is related to the glucosinolate content of the seed. While the leachates of alfalfa seed, the primary raw material of the green sprouts industry, actually stimulate the growth of *Escherichia coli*, leachates of cruciferous seeds (e.g., broccoli, cauliflower, kale, daikon, cabbage, arugula) contain glucosinolates and their isothiocyanate congeners (e.g., glucoraphanin and sulforaphane), which inhibit the growth of *E. coli*. Thus, glucoraphanin and its isothiocyanate congener, sulforaphane, not only induce Phase 2 enzymes of xenobiotic detoxification in mammals, and are chemoprotective, but they are also antimicrobial.

However, leakage during imbibition reduces the glucosinolate content of seeds and sprouts, thereby reducing their antibiotic and anti-carcinogenic activity. Furthermore, current commercial green sprout production systems result in only very low antibiotic activity of the leachate as well.

Thus, there is a need in the art to identify particular crucifer plants that yield high levels of Phase 2 enzyme-inducer activity for chemoprotection. There is also a need to identify crucifer plants that produce a known spectrum of specific inducers of Phase 2 enzyme activity in order to increase the efficiency with which specific carcinogens, or classes of carcinogens, are targeted for inactivation. Furthermore, there is a need to develop germplasm which comprise increased levels of Phase 2 inducer activity and to develop methods which effectively and efficiently manipulate the spectrum of inducers produced in particular varieties and lines. Finally, there is a need to obtain seeds and sprouts which exhibit decreased leakage of glucosinolates upon germination and sprouting. There is also a need to develop methods for commercial green sprout production which result in increased antibiotic production in the leachate without significantly decreasing the chemoprotectant activity present in the market sprout tissue.

It is therefore desirable to obtain crucifer varieties which possess consistent qualities and quantities of chemoprotectant activity. It is also desirable to obtain crucifer varieties which produce high levels of antibiotic activity during the sprouting process thereby reducing the risk the sprouts will become contaminated with human pathogens. It is also desirable to obtain crucifer varieties which also possess high quality chemoprotectant activity. Such crucifer varieties include open-pollinated and inbred broccoli and cauliflower lines which contain high levels of alkylthioalkyl glucosinolates relative to the levels of indole glucosinolates.

It is further desirable to obtain crucifer seeds and sprouts which exhibit decreased leakage of glucosinolates upon germination and sprouting. It is also desirable to obtain commercial green sprout production methods which result in increased antibiotic production in the leachate without significantly decreasing the chemoprotectant activity present in the market sprout tissuse.

SUMMARY OF THE INVENTION

Enhancing the anticancer qualities of cruciferous vegetables, seeds, and sprouts can be accomplished by the development of novel germplasm, using techniques of the instant invention.

It is therefore an object of the present invention to provide methods for developing novel crucifer germplasm, particularly broccoli and cauliflower germplasm, that contains significant quantities of,cancer chemoprotective compounds.

Another object of the present invention is to provide methods for developing novel crucifer germplasm, particularly broccoli and cauliflower germplasm, which contain substantial quantities of Phase 2 enzyme-inducers and are essentially free of Phase 1 enzyme-inducers.

It is a further object of the present invention to provide methods for developing crucifer germplasm, particularly broccoli and cauliflower germplasm, which contain substantial quantities of Phase 2 enzyme-inducing potential and non-toxic levels of indole glucosinolates and their breakdown products. Such germplasm contains an enhanced ratio of indole/alkyl glucosinolates in the appropriate tissue which is ultimately destined for the market and subsequent use. This tissue includes seeds, sprouts, and market-stage heads.

It is also an object of the present invention to provide methods for the creation of novel inbred or doubled haploid crucifer germplasm, particularly broccoli and cauliflower germplasm, by selecting for enhanced alkylthioalkyl/indole glucosinolate ratios.

It is also an object of the present invention to provide novel inbred or doubled haploid crucifer germplasm, particularly broccoli and cauliflower germplasm, which comprise enhanced alkylthioalkyl/indole glucosinolate ratios.

It is yet a further object of the present invention to provide methods for developing novel crucifer germplasm, particularly broccoli and cauliflower germplasm, with seeds of reduced leaching capacity and higher glucosinolate content.

It is also an object of the present invention to provide a method of germinating cruciferous seeds and sprouts under conditions which increase antibiotic activity against a range of human pathogens, and which increase the chemoprotectant activity of the sprouts.

These objects, and others, are achieved by providing a method of developing novel crucifer germplasm, particularly broccoli and cauliflower germplasm, with enhanced chemoprotectant properties, comprising (1) providing a population of doubled haploid plants, and (2) selecting an individual plant with an enhanced alkyl/indole glucosinolate ratio. Alternatively or in addition, the individual plant also produces seeds with reduced leakage of seed material upon germination and sprouting, resulting in higher glucosinolate content. The population of doubled haploid plants may be obtained from a parent plant by anther culture techniques.

The selecting step may comprise screening each plant to determine its alkyl/indole glucosinolate ratio. Furthermore, the screening step may comprise the steps of preparing an extract from a plant, and measuring the amount of alkyl and indole glucosinolates in said extract. Finally, the screening step may comprise screening the seed produced by each plant to determine the amount of leakage of material from the seed, and the glucosinolate content present in both the seeds themselves and in such leakage.

Also provided is a method for developing a novel inbred crucifer germplasm, particularly broccoli and cauliflower germplasm, with enhanced chemoprotectant properties, comprising (1) providing a population of doubled haploid plants, (2) selecting an individual plant with an enhanced alkyl/indole glucosinolate ratio, and (3) selfing the selected plant, and selecting the progeny from the selfed plant with an enhanced alkyl/indole glucosinolate ratio. Alternatively, or in addition, the individual plant also produces seeds of reduced leaching capacity resulting in higher glucosinolate content. Progeny from the selfed plant also produce seeds of reduced leakage of seed material.

Also provided is a method for creating novel inbred crucifer germplasm with enhanced chemoprotectant properties, comprising the steps of (1) providing a population of mutagenized plants, and (2) selecting an individual plant with an enhanced alkyl/indole glucosinolate ratio. Alternatively, or in addition, the individual plant also produces seeds of reduced leaching capacity resulting in higher glucosinolate content.

Also provided is a crucifer variety which comprises an enhanced alkyl/indole glucosinolate ratio, wherein said enhanced ratio is greater than about 10%, more preferably 20%, most preferably 30% or greater, of the ratio observed in the parent plant from which the variety is developed. Alternatively, or in addition, the crucifer variety produces seeds with reduced leakage of seed material upon germination and sprouting.

Also provided is a method of germinating cruciferous seeds and sprouts under conditions which increases antibiotic activity in the sprouting environment, and which increases the chemoprotectant activity of the sprouts, by imbibing and germinating the seeds in a ratio of water to dry seed which is just sufficient to permit normal growth of the sprouts over the normal commercial sprouting period and which does not result in any appreciable run-off from the sprouts.

Thus, the present invention is directed to a method for selecting a plant comprising measuring the ratio of alkyl glucosinolate to indole glucosinolate content in a tissue of a plant, and selecting the plant if the ratio is a specific number. Preferably, the plant is a double haploid plant such as one obtained by an anther culture technique, or a mutagenized plant such as a plant mutagenized with a chemical mutagen (e.g., ethylmethane sulfonate), wherein the plant is mutagenized before the measuring step.

Advantageously, the plant is a crucifer such as broccoli, preferably belonging to a cultivar selected from the group consisting of Saga, DeCicco, Everest, Emerald City, Packman, Corvet, Dandy Early, Emperor, Mariner, Green Comet, Green Valiant, Arcadia, Calabrese Caravel, Chancellor, Citation, Cruiser, Early Purple Sprouting Red Arrow, Eureka, Excelsior, Galleon, Ginga, Goliath, Green Duke, Greenbelt, Italian Sprouting, HiSierra, Late Purple Sprouting, Late Winter Sprouting White Star, Legend, Leprechaun, Marathon, Mariner, Minaret (Romanesco), Paragon, Patriot, Premium Crop, Rapine (Spring Raab), Rosalind, Salade (Fall Raab), Samurai, Shogun, Sprinter, Sultan, Taiko, and Trixie, and Viking.

Alternatively, the plant is a crucifer such as cauliflower, preferably belonging to a cultivar selected from the group consisting of Alverda, Amazing, Andes, Burgundy Queen, Candid Charm, Cashmere, Christmas White, Dominant, Elby, Snowball and selections of Snowball, Fremont, Incline, Milkyway Minuteman, Rushmore, S-207, Serrano, Sierra Nevada, Siria, Snow Crown, Snow Flake, Snow Grace, Snowbred, Solide, Taipan, Violet Queen, White Baron, White Bishop, White Contessa, White Corona, White Dove, White Flash, White Fox, White Knight, White Light, White Queen, White Rock, White Sails, White Summer, White Top, and Yukon.

The present invention is also directed to a method for producing a progeny plant comprising measuring the ratio of alkyl glucosinolate to indole glucosinolate content in a tissue of a potential parent plant, selecting the potential parent plant if the ratio is a specific number, and producing a progeny plant from the selected plant. Advantageously, the ratio of alkyl glucosinolate to indole glucosinolate in a tissue of the progeny plant is higher than the ratio of alkyl glucosinolate to indole glucosinolate in a tissue of the selected plant, and the tissue of the progeny plant and the tissue of the selected plant is of the same type. The present invention is also directed to a progeny plant produce by this method.

In preferred embodiments, the ratio in the tissue of the progeny plant is at least 10%, 20%, 30%, 50%, or 100% greater than the ratio in the tissue of the selected plant. In another preferred embodiment, the ratio in the tissue of the progeny plant is at least 10 times or 100 times as great as the ratio in the tissue of the selected plant. In yet another preferred embodiment, the ratio in the tissue of the progeny plant is between 10% greater than and 100% greater than, 20% greater than and 80% greater than, or 30% greater than and 60% greater than, the ratio in the tissue of the selected plant. In yet another preferred embodiment, the ratio in the tissue of the progeny plant is between 10 times as great and 100 times as great, or between 25 times as great and 75 times as great, as the ratio in the tissue of the selected plant. Advantageously, the progeny plant is produced by selfing the selected plant, or the progeny plant is a hybrid plant.

The present invention is also directed to a cruciferous plant, such as a broccoli plant or a cauliflower plant, wherein the ratio of alkyl glucosinolate to indole glucosinolate in a tissue of the plant is greater than 6, 10, 25, 50, 100, or 1000. In a preferred embodiment, the ratio of alkyl glucosinolate to indole glucosinolate in a tissue of the plant is between 6 and 1000, 10 and 500, 25 and 250, or 50 and 100.

The present invention is also directed to a method for selecting a seed or sprout comprising (a) adding a quantity of water to a seed or sprout, (b) measuring the concentration of glucosinolates in the leachate of the seed or sprout, and (c) selecting the seed or sprout if the concentration is a specific value.

The present invention is also directed to a method for producing a progeny plant comprising (a) adding a quantity of water to a seed or sprout, (b) measuring the concentration of a glucosinolate in the leachate of the seed or sprout, (c) selecting the seed or sprout if the concentration is a specific value, and (d) producing a progeny plant from the selected seed or sprout.

The present invention is also directed to a method for inhibiting or preventing the growth of a microbe in an environment capable of sustaining the microbial growth comprising administering to the environment a microbial growth-inhibiting amount of a cruciferous seed leachate or a cruciferous sprout leachate. Advantageously, the microbe is a bacterium such as Escherichia (e.g., *Escherichia coli*) or Staphylococcus (e.g., *Staphylococcus aureus*). Preferably, the leachate is a broccoli leachate or a cauliflower leachate. Ideally, the leachate contains a glucosinolate or an isothiocyanate.

The present invention is also directed to a method for preparing sprouts comprising (a) providing a quantity of seeds, (b) adding to the seeds between 0.6 and 1.0 g of water per g of seeds, (c) allowing the watered seeds to germinate and form sprouts, and (d) adding to the sprouts between 5 and 9 mg of water per sprout per 24 h for 24 to 120 h, thereby preparing the sprouts. Preferably, step (b) comprises adding to the seeds between 0.7 and 0.9 g (ideally 0.8 g) of water per g of seeds. Preferably, step (d) comprises adding to the sprouts between 0.6 and 0.8 mg (ideally 0.7 mg) of water per sprout per 24 h for 24 to 120 h. Preferably, step (d) comprises adding to the sprouts between 0.5 and 0.9 mg of water per sprout per 24 h for 48 to 120 h (ideally 72 h). Advantageously, the sprouts are cruciferous sprouts such as broccoli sprouts or cauliflower sprouts.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENT

1. Definitions

In the description that follows, a number of terms are used extensively. The following definitions are provided to facilitate understanding of the invention.

Anther culture is the in vitro culture of anthers to obtain haploid or homozygous regenerated plants. The anthers contain microspores or immature pollen grains which, when grown on nutrient medium under the appropriate conditions, give rise to embryos which in turn can be regenerated into plants. Because the cultured microspore cells and immature pollen grains are derived from cells which underwent meiosis, their chromosome number is half that of the parent plant, and the plants regenerated from these cultured cells are therefore haploid.

A chemoprotector or chemoprotectant is a synthetic or naturally occurring chemical agent that reduces susceptibility in a mammal to the toxic and neoplastic effects of carcinogens.

A doubled haploid is a diploid plant produced by doubling the chromosome content of a haploid plant. Typically, a haploid plant is obtained from anther culture; the chromosomes are doubled either artificially, as by treatment with colchicine, or spontaneously. A doubled haploid is homozygous at all genetic loci.

An enhanced alkyl/indole glucosinolate ratio is a ratio which is greater than that observed in about 70%, preferably 80%, most preferably 90% of a tested population of plants, or which is greater than that observed in the parent(s), preferably at least 20% greater, from which a tested plant is derived. Alternatively, an enhanced ratio is one which does not occur naturally, in that it is artificially induced, as by mutagenesis treatment or somaclonal variation during tissue culture, and which is significantly greater than that which occurs generally in the population of plants from which the treated plants are derived.

A glucosinolate profile is a determination of both the types of glucosinolates, and the amount of each type of glucosinolate, measured in a plant. A glucosinolate profile may be determined by measuring the amounts of alkyl and indole glucosinolates, and determining the ratio of alkyl to indole glucosinolate.

Inducer activity or Phase 2 enzyme-inducing activity is a measure of the ability of a compound(s) to induce Phase 2 enzyme activity. (See Prochaska and Santamaria (1988) *Anal. Biochem.* 169: 328–336 and Prochaska et al. (1992) *Proc. Natl. Acad. Sci. USA* 89: 2394–2398).

An inbred or breeding line is a plant line which is homozygous, or nearly so. Typically, such lines were produced by conventional plant breeding techniques; however, more recently such lines may be obtained through tissue culture techniques such as doubled haploid production. Inbred lines are used for producing hybrids.

Inducer potential or Phase 2 enzyme-inducing potential is a measure of the combined amounts of inducer activity in plant tissue provided by isothiocyanates, plus glucosinolates that can be converted by myrosinase to isothiocyanates. Glucosinolates are not themselves direct inducers of mammalian Phase 2 enzymes; instead, their metabolic products, isothiocyanates, are inducers.

A cultivar, or variety, is a group of similar plants which belong to the same species and which by structural features and performance may be distinguished from other varieties within the same species. Two essential characteristics of a variety are identity and reproducibility. Identity is necessary so that the variety may be recognized and distinguished from other varieties within the crop species. The distinguishing features may be morphological characteristics, color markings, physiological functions, disease reaction, or performance. Most agricultural varieties are pure for those characteristics which identify the variety. Reproducibility is needed so that the characteristics by which the variety is identified will be reproduced in the progeny. A variety is derived from a strain; populations which are increased from a single genotype or a mixture of genotypes are referred to as strains, experimental strains, or lines. Once a strain is identified as superior, it may be named, increased, and made available commercially as a "cultivated variety," or "cultivar." The words "variety" and "cultivar" are used interchangeably, although cultivar is commonly used in scientific literature while variety is the term used by U.S. farmers and the seed trade.

2. Description

A major mechanism of protection provided by crucifer plants in reducing the incidence of cancer in humans depends on the presence in the plant tissue of minor chemical components which, when delivered to mammalian cells, elevate levels of Phase 2 enzymes that detoxify carcinogens. It has now been discovered that the anticarcinogenic activity of crucifer plants can be increased by developing novel inbred lines with enhanced chemoprotectant activity. The enhanced chemoprotectant activity is due to an enhanced alkyl to indole glucosinolate ratio. Such an enhanced ratio can be achieved, for example, by a quantitative increase in the level of specific alkyl glucosinolates, such as akylthioalkyl glucosinolates, or by a quantitative decrease in the level of indole glucosinolates. The chemoprotectant activity of market sprout tissue may also be enhanced by developing novel inbred crucifer lines which produce seeds with decreased leakage of seed material.

Furthermore, it has been discovered that if the amount of water supplied to developing crucifer sprouts is minimized or reduced to a level which keeps the developing sprouts moist but not dripping wet, the concentrations of such antibiotics in the leachate are increased, such that inhibitory effects against potentially contaminating microbes, including human pathogens and food poisoning organisms such as E. coli, Salmonella spp., and Listeria spp., are enhanced. On the other hand, growing such sprouts with reduced watering leads to reduced leaching of glucosinolates, as well as other inorganic ions and organic compounds, which results in enhanced levels of these compounds in the plant tissue which is ultimately consumed. Thus, for example, levels of glucoraphanin, which exhibits cancer preventive properties, can be enhanced in sprout tissue germinated with reduced amounts of water.

Methods of developing such novel germplasm include combining novel screening techniques to identify and select plant tissue with enhanced alkyl to indole glucosinolate ratio with conventional and unconventional breeding techniques. In particular, such methods result in crucifer varieties, more particularly broccoli and cauliflower varieties, with enhanced tissue ratios of alkyl/indole glucosinolates. Alternatively, or in addition, screening includes evaluating seeds with reduced leakage of seed material upon germination and sprouting, and in particular with reduced leakage of glucosinolates from the seed.

Crucifer plants to be used in the claimed methods for producing plants with an enhanced ratio of alkyl/indole glucosinolates are from the family Cruciferae, of the tribe Brassiceae, and the subtribe Brassicinae. Preferably, the crucifer plants are from the *Brassica oleracea* group and include *acephala* (kale, collards, wild cabbage, curly cale), *medullosa* (marowstem kale), *ramosa* (thousand head kale), *alboglabra* (Chinese cale), *botrytis* (cauliflower, sprouting broccoli), *costata* (Portuguese kale), *gemmifera* (Brussel sprouts), *gongylodes* (kohlrabi), *italica* (broccoli), *palmifolia* (Jersey kale), *sabauda* (savoy cabbage), *sabellica* (collards), *selensia* (borecole), and *capitata* (cabbage), among others. Other crucifer plants that can be used in the claimed methods for producing plants with an enhanced the ratio of alkyl/indole glucosinolates include *Lepidium sativum* (cress), *Sinapis alba* and *S. niger* (mustard), *Raphanus sativum* (radish daikon), *Eruca sativa* (arugula), among others, as can cross-variety, -species or -genera hybrids thereof.

Screening: Glucosinolate Profile

In order to screen large numbers of individual plants to select those plants with an enhanced alkyl/indole glucosinolate ratio, it was necessary to develop improved techniques for isolating, identifying, and quantitating the different types of glucosinolates present in the plant extracts.

Separation of individual glucosinolates is difficult because these molecules are highly charged and water-soluble; resolution of the different molecules depends on the properties of the less polar side chains. Many less than ideal chromatographic methods have been developed for the isolation and separation of glucosinolates. (See, for example, Betz, J M and Fox, W D (1994) in FOOD PHYTOCHEMICALS FOR CANCER PREVENTION. I. FRUITS AND VEGETABLES, Huang, M T et al. (eds) ACS Symposium Series, 546, pp 181–196, Am Chem Soc, Washington, D.C.; Heaney, R K and Fenwick, G R (1987) in GLUCOSINOLATES IN RAPESEEDS: ANALYTICAL ASPECTS, Wathelet, J P (ed), pp 177–191, Nijhoff Dordrecht, The Netherlands; Wathelet, J P (1987) GLUCOSINOLATES IN RAPESEEDS: ANALYTICAL ASPECTS, Nijhoff Dordrecht, The Netherlands). These chromatographic methods include ion exchange, gas liquid chromatography (GLC), and high pressure liquid chromatography (HPLC), most of which involve chemical modification by enzymatic sulfate removal and/or silylation.

Recently, a simple and direct strategy for analyzing the glucosinolate content of plant extracts was developed; this strategy involved a new combination of widely available techniques. (Prestera, T et al. (1996) Anal. Biochem. 239: 168–179; reference incorporated herein in its entirety.) The analytical strategy also provided a powerful technique for identification and quantification of glucosinolates in plant extracts without resorting to derivitization.

Plant extracts are prepared by homogenizing plant tissue with 10 vol. of a mixture of equal volumes of dimethyl sulfoxide, dimethylformamide, and acetonitrile (triple solvent) maintained at about −50° C. in a dry-ice/ethanol bath. Samples are homogenized, depending on sample size, in a glass homogenizer, a Brinkmann Polytron homogenizer, or a Waring Blender. Other extractive solvents include boiling methanol, boiling water, ice-cold water, and acetonitrile. For example, plant extracts may also be prepared by immersing harvested plant tissue in boiling water, followed after a short period of time by homogenization. In all cases, the homogenates are centrifuged, and the supernatant is optionally filtered to remove remaining particulates. The resulting crude aqueous extract may be stored at −20 to −80° C. until analyzed.

Intact glucosinolates from the crude plant extracts are then isolated, identified, and quantitated by sequential analysis. The procedure entails reverse-phase paired ion chromatography (PIC) of the hydrophobic tetraakylammonium salts of the glucosinolates in the presence of an excess of these counterions, conversions of these glucosinolate salts to their ammonium salts, direct negative-ion fast atom bombardment (FAB) spectroscopic and ammonia chemical ionization (CI) mass spectroscopic analysis, and finally high resolution nuclear magnetic resolution (3H NMR) spectroscopy. Details are provided by Prestera, T et al. (1996) Anal. Biochem. 239: 168–179, which is incorporated by reference in its entirety.

Preferably, plant extracts are chromatographed in acetonitrile/water (1:1, vol./vol.) containing 5 mM tetradecylammonium bromide at a flow rate of 3 ml/min., on reverse-phase columns (Whatman Partisil 10 ODS-2; 250×4 mm) on a Waters HPLC system equipped with a photodiode array detector (see Prestera, T., et al. (1996) Anal. Biochem. 239: 168–179). Sinigrin (allyl glucosinolate) is used as a standard. The relative integrated absorbance areas at 235 nm for alkylthioglucosinolates such as glucoraphanin, glucobrassicin, and neoglucobrassicin are 1.00, 1.22, and 2.70 times, respectively, those of an equimolar quantity of sinigrin (Fahey J W et al. (1997) Proc. Natl. Acad. Sci. USA 94: 10367–10372; Shapiro T A et al. (1998) Cancer Epidemiol. Biomark. Prevent. 7:1091–1100).

The tissue sampled depends upon the objectives of the breeding program; thus, the sampled tissue may include market stage heads, which are flower buds before they open, leaf tissue, seed tissue, and/or sprout tissue. When breeding for a desirable glucosinolate profile in market stage heads, the flower bud tissue is preferably sampled before the buds have opened.

Screening: Seed Leachate

Seeds of individual plants may be screened for the amount of leakage of seed material during germination and sprouting, and in particular for the amount and type of glucosinolate released into the leachate.

Seeds are first disinfected, typically with a bleach solution of about 20% bleach in water, and then rinsed thoroughly with water, according to commonly used protocols in the sprouting industry. The seeds are then placed in germination containers; such chambers may consist of flat trays, which may be inclined, or they may be containers suitable for shipping and marketing. Typically, the latter type of container is a plastic box or jar which contains a water pad at the bottom. These containers allow light to penetrate while providing a mechanically protective barrier. Such trays or containers are preferably designed or modified or shaped to allow rinsing of the germinating seeds and collecting of the resulting rinse solution, or leachate, while promoting normal growth of the sprouts during normal commercial growth period. Numerous methods for the cultivation of sprouts are known, as exemplified by U.S. Pat. Nos. 3,733,745, 3,643,376, 3,945,148, 4,130,964, 4,292,760, or 4,086,725.

The seeds are then rinsed with defined amounts of water for defined periods at determined intervals; this rinse water, or leachate, is then collected and the content of seed material in the leachate determined. Various well-known methods for measuring leaked or released seed material, including total dry weight and determination of released proteins and sugars, may be used. In addition or alternatively, the amount and profile of released glucosinolates may be determined, as described above.

Selection

The objectives of the breeding program will determine which plants are subjected to the screening program, and which plants are selected for further breeding. Other factors to be considered are which tissues are to be sampled, and at what stage; thus, some programs may be directed toward market vegetable products, such as broccoli and cauliflower heads or florets, while others may be directed toward niche market products such as sprouts or more mature plant parts from which teas, effusions, decoctions or extracts of desirable qualities can be prepared.

Different types of plant populations may be screened, depending on the type of germplasm and the subsequent breeding strategies. Preferably, a population of homozygous plants are screened; such homozygous plants are most likely to have been developed by tissue culture techniques, but they may also have been developed by conventional breeding techniques. Other preferred populations of plants suitable for screening include those plants which have been subjected to mutagenesis.

Tissue culture techniques, which can be used to give rise to homozygous plants, include in vitro culturing anthers containing microspores or immature pollen grains on a nutrient medium for the purpose of generating haploid plantlets. The chromosome number of the recovered haploid plantlet is then doubled by an appropriate procedure to produce a completely homozygous diploid plant, referred to as a doubled haploid plant.

Doubled haploid plants which are selected as desirable through the screening program are increased and further evaluated for agronomic characteristics. Alternatively, the plant increases are utilized immediately as inbred lines in hybrid breeding for cross-fertilizing plants. The time required to produce a cultivar or inbred line by this procedure is reduced by several generations, as compared to that required by conventional breeding.

Anther culture techniques for broccoli tissue are well-known in the art (Keller, W A et al (1975) *Can. J. Genet. Cytol.* 17: 655–666; Keller, W A and Armstrong, K C (1988) *Euphytica* 32: 151–159; Arnison, P G et al (1990) *Plant Cell, Tissue and Organ Culture* 20: 147–155; Arnison, P G et al (1990) *Plant Cell, Tissue and Organ Culture* 20: 217–222; Chiang, M S (1985) *Can. J. Plant Sci.* 65: 1033–1037). In general, the technique involves selecting buds from the main inflorescence prior to flower emergence, surface sterilizing the buds, and plating the tissue on culture medium. Embryos are generated from microspores, and subsequently regenerated into plants. Under the reported culture conditions, about half of the plants are doubled haploids, while the remainder are haploid, tetraploid, and other ploidy. Identification of the doubled haploids can be accomplished by DNA flow cytometry (Arumaganathan, K. and Earle, ED (1991) *Agronomie* 11: 727–736). The chromosome number in the haploid plants can be doubled by appropriate treatment, as for example by treatment with colchicine using methods well known in the art, or the chromosome number may double spontaneously.

The glucosinolate profile can be altered by decreasing or knocking out the synthesis of indole glucosinolates, or by increasing the synthesis of alkyl glucosinolates. There are several techniques for achieving this goal. For example, one method is simply to utilize somaclonal variation which occurs during tissue culture. Another method is to subject plants to mutagenesis treatments to increase the frequency of the appearance of plants with a desirable glucosinolate profile. Yet another method is to inactivate or knock out the genes involved in indole glucosinolate synthesis, such as by insertion of DNA into these genes.

Mutagenesis treatments include ionizing radiations and chemical mutagens, although the latter are currently preferred. The most widely used chemical is ethyl methane sulfonate (EMS). Although seeds are most commonly treated, pollen, living plants, or parts of the plant, including buds, roots, and dormant cuttings, may also be treated. Treatment generally consists of soaking the plant or plant parts in a solution of a chemical mutagen. The treated plant material is then used to generate whole plants which are then subjected to screening and selection procedures. Plant mutagenesis methods are well known in the art. See, for example, Malmberg, R. L., "Production and Analysis of Plant Mutants Emphasizing *Arabidopsis thaliana*" in METHODS IN PLANT MOLECULAR BIOLOGY AND BIOTECHNOLOGY, B. R. Glick and J. E. Thompson, Eds. (CRC Press, Boca Raton 1993).

Inactivation or knockout of genes involved in indole glucosinolate synthesis by DNA insertion of a mobile DNA sequence, such as T-DNA or transposons, from the host plant or from a heterologous origin, are techniques well known in the art (Koncz et al., 1992). T-DNA insertion may be carried out by known methods via Agrobacterium (Hoekema et al., 1983; U.S. Pat. No. 5,149,645) and transposon insertion may be done by well known methods (Fedoroff et al., 1984; U.S. Pat. Nos. 4,732,856 and 5,013,658). The transposable element used may be an autonomous transposon, a non-autonomous transposon, or an autonomous/non-autonomous transposon system, e.g. the maize Ac/Ds transposon system.

Preferably, plants selected for screening are those with desirable agronomic characteristics. However, if less desirable plants are selected for screening, the trait of desirable glucosinolate profile can be introduced into commercially desirable varieties by conventional breeding techniques.

It is also preferred that plants selected for screening be grown under similar conditions and be harvested at similar stages of development. This facilitates comparison among different individual plants, as both the quantity and quality of glucosinolates is known to vary among different plant tissues and at different stages of development, and to vary upon different growing conditions. The parts of the plants selected for screening include seeds, sprouts, and florets. The tissue chosen depends upon the ultimate market for which the germplasm is being developed. Depending upon the choice of tissue for screening, different individual plants may be selected, as the glucosinolate profile in each tissue may vary within one plant, and there appears to be no correlation among the different tissue profiles. For example, a plant with a market stage head tissue which possesses a desirable glucosinolate profile may have a sprout with an undesirable, or less desirable, glucosinolate profile, or has a total levels of alkylthioalkyl glucosinolates that are very low compared to other cultivars.

Those plants which exhibit a desirable glucosinolate profile in the appropriate tissue for the end market are selected for subsequent development. A preferred profile is an enhanced alkyl/indole glucosinolate ratio. An enhanced ratio is a ratio which is greater than that observed in about 70%, preferably 80%, most preferably 90% of the tested population of plants. Alternatively, an enhanced ratio is a ratio which is greater than the ratio observed in the parent plant, preferably 10% greater, more preferably at least 20% greater, most preferably at least 30% greater. Alternatively, an enhanced ratio is one which does not occur naturally, in that it is artificially induced, as by mutagenesis treatment or somaclonal variation during tissue culture, and which is significantly greater than that which occurs generally in the population of plants from which the treated plants are derived.

Alternatively or in addition, those plants which produce seeds with decreased leakage of seed material during germination and sprouting, and in particular with decreased glucosinolate leakage, are selected for further development. Decreased leakage is defined as a significant decrease when compared to leakage observed for the parent plant, or when compared to the leakage observed for the plant population from which the individual plant is obtained. Significant decrease is a decrease of at least 10%, preferably 30%, most preferably 50% or more, of the leakage observed for the parent plant. Alternatively, a significant decrease in leakage is leakage which is observed in only 10%, preferably 5%, or most preferably 1% of the plant population. Alternatively, significant decrease is one which does not occur naturally, in that it is artificially induced, as by mutagenesis treatment or somaclonal variation during tissue culture, and which is a significantly smaller amount of leakage than that which occurs generally in the population of plants from which the treated plants are derived.

Plant Breeding

Once individual plants possessing desirable glucosinolate profiles are selected, they are used for further development. The enhanced alkyl/indole glucosinolate ratios may occur in market stage heads, sprouts, seeds, or other plant parts. The following breeding procedures may be applied to plants which are doubled haploids, mutagenized plants, or other source plants screened for glucosinolate profiles.

In general, breeding is effected by screening progeny of the selected plants for the trait of enhanced alkyl/indole glucosinolate ratios (as described above), where the ratios are produced in the desired plant parts at the desired plant developmental stages. Plants carrying this trait are further developed by intensifying the trait or by combining the trait with other important agronomic characteristics. Thus, plants with the selected trait may be used directly to establish new varieties, or they may be used as a source to transfer the trait into other agronomically desirable varieties.

Particularly useful broccoli varieties to be used in the claimed method are Saga, DeCicco, Everest, Emerald City, Packman, Corvet, Dandy Early, Emperor, Mariner, Green Comet, Green Valiant, Arcadia, Calabrese Caravel, Chancellor, Citation, Cruiser, Early Purple Sprouting, Red Arrow, Eureka, Excelsior, Galleon, Ginga, Goliath, Green Duke, Greenbelt, Italian Sprouting, Late Purple Sprouting, Late Winter Sprouting White Star, Legend, Leprechaun, Marathon, Mariner, Minaret (Romanesco), Paragon, Patriot, Premium Crop, Rapine (Spring Raab), Rosalind, Salade (Fall Raab), Samurai, Shogun, Sprinter, Sultan, Taiko, Late Purple Srouting, Light Star, and Trixie. However, many other broccoli varieties are suitable.

Particularly useful cauliflower varieties are Alverda, Amazing, Andes, Burgundy Queen, Candid Charm, Cashmere, Christmas White, Dominant, Elby, Snowball and Snowball selections, Fremont, Incline, Milkyway Minuteman, Rushmore, S-207, Serrano, Sierra Nevada, Siria, Snow Crown, Snow Flake, Snow Grace, Snowbred, Solide, Taipan, Violet Queen, White Baron, White Bishop, White Contessa, White Corona, White Dove, White Flash, White Fox, White Knight, White Light, White Queen, White Rock, White Sails, White Summer, White Top, Yukon. However, many other cauliflower varieties are suitable.

The goal of the breeding program is to ensure that the selected glucosinolate profile trait is stable, that it exists in plants with desirable agronomic characteristics or can be transferred into such plants, and that the selected plants can be used to develop varieties or lines from which marketable hybrid seed can be created.

To ensure that the enhanced glucosinolate trait is stable, an F1 generation is obtained from the selected plants. Although several approaches are feasible, it is preferable to self-pollinate the selected plants to establish an F1 progeny generation which can be screened for glucosinolate profiles. Because broccoli and cauliflower are self-incompatible plants, the selected plants may be artificially self-pollinated by several techniques. One technique is "bud pollination," which involves placing pollen on immature stigmas 1–2 days prior to anthesis. The buds are carefully opened with forceps and pollen from mature flowers is placed on the immature stigmas. Another technique is to pretreat mature stigmas with NaCl or $CO_2$. Mature stigmas may be exposed to 15% NaCl for 10–15 minutes prior to pollination, or they may be exposed to increased $CO_2$ levels (preferably 5% $CO_2$) for a few hours prior to pollination.

The resulting F1 seed is collected, and grown into mature plants which are then screened for glucosinolate profiles. Those plants in which the trait of enhanced glucosinolate profile is stable are selected for further breeding. Such breeding includes development of inbred lines from the selected plants, or further developing the selected plants by selecting for other agronomic traits or by introgressing the trait into other desirable lines or varieties. Strategies for the crossing, selection and breeding of new varieties of Cruciferae are well known. (See *Brassica Crops and Wild*

*Allies: Biology & Breeding*; S. Tsunoda et al. (eds), Japan Scientific Societies Press, Tokyo pp. 1–354 (1980)).

Those plants which are derived from doubled haploid plants obtained from anther culture give rise to "instant inbreds," as the doubled haploid is already homozygous at every genetic locus. Use of these plants in breeding can result in the production of inbred lines in 2 years instead of the 5 years required in conventional breeding programs (Ockendon, D. J. (1986) in GENETIC MANIPULATION IN PLANT BREEDING, Horn, J. et al. (eds) De Gruyter, New York, pp. 265–272). Such lines may themselves be used as new cultivars, or as parents to produce hybrids.

The inbred parents, however, are difficult to maintain because they are self-incompatible. Therefore, various methods are used to overcome the self-incompatibility system. One set of such methods is directed to seed production. These methods include alteration of nutritional conditions (Stout, A. B. (1931) *Am J Bot* 18: 686–695), pollen transplantation (Kroh, M. (1966) (Contribution to characterization of the incompatibility mechanisms with Cruciferae), Z üchter Vol. 36: 185–189), mutilation of the stigma (Linskens, H. F. and Kroh, M. (1967) *Handb Pflanzenphysiol* Vol. 18: 506–530), chemical treatments (Tatebe, T. (1968) *J Jpn Soc Hortic Sci.* 37: 227–230), $CO_2$ treatment (Nakanishii, et al. (1968) *Plant Cell Physiol* 10: 925–927), high temperatures (Gonai, H. and Hinata, K. (1971) *L Jpn J Breed* 21: 195–198), and electrical treatment (Roggen, et al. (1972) *L Euphytica* 21: 181–184). The method routinely used, however, is pollination of buds before the self-incompatibility is effective, or "bud pollination" (Wiering, D. (1958) *Euphytica* 7: 223–227).

Seed production by these methods, however, is laborious and expensive. A second set of methods to overcome the self-incompatibility system is directed to vegetative propagation to maintain the inbred lines. These methods include propagation from vegetative plant parts such as stem, leaf, and rib explants (Johnson, et al. (1970) *Hort Sci* 13: 246–247), propagation from stem cuttings and whole or parts of the sprout buttons (Nieuwhof, M. (1969) in WORLD CROPS SERIES, Hill, London), and propagation from root cuttings (North, C. (1953) *Ann Appl Biol* 40: 250–261). These methods can also be used for propagating plants selected from field trials.

The trait of enhanced glucosinolate profiles is introgressed into lines of superior agronomic performance by conventional breeding techniques. Such techniques include recurrent selection (Vello, et al. (1977); ESALQ, Piracicaba, Brazil, p. 742; (1978) Plant Breed Abstract Vol. 48, p. 7062) and additive genetic variation by inbreeding for uniformity and combining inbred lines as synthetics (Honma, S. (1965) *J Am Soc Hortic Sci* 87: 295–298). Heterosis (Legg, et al. (1968) *J Am Soc Hortic Sci* 92: 432–437) is exploited by the breeding of Fi hybrid cultivars. Cytoplasmic male sterility (cms), which is now available in calabrese (Dickson, M. H. (1975) *HortSci* 10: 535), is used to breed hybrids.

The same breeding techniques may be applied to developing lines which produce seeds with decreased leadkage of seed material, and especially of glucosinolates, during germination and sprouting.

Seed Germination with Decreased Leakage of Seed Material

Another method by which to minimize leakage of seed material, and especially glucosinolates, during seed germination and sprouting, is to imbibe and germinate the seeds in a ratio of water to dry seed which is just sufficient to permit normal growth of the sprout over the normal commercial sprouting period, and which does not result in any water run-off from the sprouts. The exposure of the seeds to a decreased volume of water decreases the amount of seed material, and in particular of glucosinolates, leaked from the seed during germination and sprouting. The decreased leakage results in increased retention of glucosinolates, resulting in a sprout with enhanced chemoprotectant properties. Furthermore, the decreased volume of water results in an increased concentration of the glucosinolates which are released, thereby increasing their antibiotic effectiveness in the sprouting environment.

Seeds are germinated as described previously, by first surface-disinfecting them and then by exposing them to defined amounts of water for defmed periods of time, over the normal commercial course of germination and sprouting. The preferred minimum volume of water is just the amount of water which allows normal growth without allowing any water to "run-off" or drip off the swelling and sprouting seeds. In common commercial practice, this amount is typically as much as 6 ml water per gm of dry seeds; water up to 15 ml per gram of dry seeds may also be used. The commercial period of germination is typically 2–5 days, and depends on the type of plant seed and sprout desired.

EXAMPLE 1

Production of Doubled Haploid Plants

Doubled haploid plants were prepared from several broccoli varieties, including Everest, HiSierra, Marathon, Sultan, and Viking by Dr. Mark W. Farnham, U.S. Department of Agriculture, Charleston, S.C., as described in Farnham, M. W., *J. Amer. Soc. Hort. Sci.* 123: 73–77 (1998), which is incorporated herein by reference. The plants were obtained by anther culture following the techniques described in Keller, WA (1984) in: CELL CULTURE AND SOMATIC CELL GENETICS OF PLANTS, Vol. 1 (Academic Press, New York), pp 302–310) which are summarized below.

Plants were grown from seeds under controlled environmental conditions. Buds were selected from the developing main inflorescence prior to stem elongation and prior to any flower emergence. The buds were surface sterilized, opened, and the anthers detached from the filament. The anthers were then planted in groups on nutrient medium solidified with agar in culture dishes. The anthers were incubated in the dark until embryoids developed from the anthers. The embryoids were then moved to continuous light to allow greening.

The young plantlets with healthy root systems were planted in pots and hardened in the greenhouse. Subsequently, the plants were planted in the field, and allowed to develop into mature plants. Market stage heads were harvested from the matured regenerated plants, and the glucosinolate content determined as follows.

EXAMPLE 2

Screening of Doubled Haploid Plants

Tissue was obtained from doubled haploid plants (DH plants), as well as from plants obtained from a pedigree selection program (F4 plants) and from hybrid plants (F1 plants). The F4 plants originated from segregating populations developed by selfing parents from the cultivars Marathon, Everest, High Sierra, and Futura. The individual F4 plants were advanced from single F2 and F3 selections, which were chosen as the best individuals, with regard to both horticultural characteristics and particularly broccoli head quality. The F1 hybrids were created by crossing two parents which were derived either sexually or from DH plants.

The glucosinolate content of the broccoli heads was determined essentially as described previously. The ratios of alkyl to indole glucosinolate was then determined for each tissue sample.

EXAMPLE 3

Results of Screening: Selection of Plants

The results of screening the DH plants, the F4 plants, and the F1 plants, are presented in Table 1.

TABLE 1

Ratio of Alkyl to Indole Glucosinolates

| CULTIVAR | PLANT | ALKYL:INDOLE |
|---|---|---|
| EVEREST | F4 | 0.02 |
| | DH | 0.04 |
| | DH | 0.11 |
| | DH | 0.11 |
| | DH | 0.11 |
| | DH | 0.13 |
| | DH | 0.15 |
| | F4 | 0.15 |
| | DH | 0.18 |
| | F4 | 0.21 |
| | DH | 0.21 |
| | DH | 0.23 |
| | DH | 0.23 |
| | DH | 0.24 |
| | DH | 0.30 |
| | DH | 0.39 |
| | DH | 0.41 |
| | DH | 0.42 |
| | F1 | 0.50 |
| | DH | 0.54 |
| | DH | 0.64 |
| | F1 | 0.80 |
| | F1 | 0.96 |
| | F1 | 0.97 |
| | F4 | 1.08 |
| HI SIERRA | DH | 0.26 |
| | DH | 0.37 |
| | DH | 0.47 |
| | DH | 0.59 |
| | DH | 0.66 |
| | DH | 0.96 |
| | DH | 1.23 |
| | DH | 1.28 |
| | DH | 1.40 |
| | DH | 1.42 |
| | F1 | 1.51 |
| | DH | 1.61 |
| | DH | 1.65 |
| | DH | 1.70 |
| | F1 | 1.74 |
| | F1 | 1.93 |
| | F1 | 2.14 |
| | DH | 2.46 |
| | DH | 2.74 |
| | F1 | 3.05 |
| | DH | 3.68 |
| | DH | 3.97 |
| MARATHON | DH | 0.23 |
| | DH | 0.27 |
| | DH | 0.42 |
| | DH | 0.50 |
| | DH | 0.51 |
| | DH | 0.57 |
| | DH | 0.60 |
| | DH | 0.60 |
| | DH | 0.62 |

TABLE 1-continued

Ratio of Alkyl to Indole Glucosinolates

| CULTIVAR | PLANT | ALKYL:INDOLE |
|---|---|---|
| | DH | 0.68 |
| | DH | 0.84 |
| | F1 | 0.91 |
| | DH | 1.38 |
| | DH | 1.54 |
| | DH | 1.64 |
| | F1 | 2.94 |
| | F1 | 3.10 |
| SULTAN | DH | 0.21 |
| | DH | 0.60 |
| | DH | 0.69 |
| | F1 | 0.71 |
| | F1 | 1.15 |
| | F1 | 1.49 |
| VIKING | DH | 0.87 |
| | F1 | 0.99 |
| | DH | 1.26 |
| | F1 | 1.35 |
| | F1 | 1.75 |
| | DH | 1.95 |
| | DH | 2.44 |
| | DH | 2.62 |

The ratio of alkyl to indole glucosinolate concentration for several cultivars of broccoli was determined. The results shown include ratios determined for several different types of individual plants including doubled haploid plants produced via anther culture ("DH"); hybrid plants created by crossing two parents which were derived either sexually or from DH plants ("F1"); and plants derived from a pedigree selection program ("F4"). These F4 plants originated from segregating populations developed from selfing parent plants derived from the indicated cultivars; the tested plants are individuals which have been selfed through 4 cycles.

As can be seen from Table 1, doubled haploid plants from two cultivars possessed alkyl to indole glucosinolate ratios that were significantly higher than those present in the other plant tested. Thus, two doubled haploid plants from HiSierra had ratios that were at least 30% higher than the highest value seen in another tested plant. Likewise, three individuals from Viking had ratios that were at least 10% higher than the highest value sent for another tested plants. These individuals are selected for further breeding.

Additionally, about 100 seeds from the same seedlot of European Sprouting Calabrese Broccoli (JHU#740) were planted in Jiffy Mix in a greenhouse. After seven days of growth, approximately 40% of a single, expanded cotyledon was cut from each planet using surgical scissors, and was immediately plunged into triple solvent at −80° C. for subsequent homogenization and paired ion chromatography HPLC for determination of glucosinolate content. Alkyl:indole ratios in these samples are listed in Table 2. The samples showed a 300-fold range of alkyl:indole ratios.

TABLE 2

Ratio of Alkyl to Indole Glucosinolates

| PLANT | TOTAL ALKYL GS$^1$/GRAM | TOTAL INDOLE GS$^2$/GRAM | ALKYL:INDOLE |
|---|---|---|---|
| 1 | 0.31 | 3.12 | 0.10 |
| 2 | 0.42 | 3.62 | 0.11 |
| 3 | 0.63 | 4.20 | 0.15 |
| 4 | 0.69 | 4.10 | 0.17 |

TABLE 2-continued

Ratio of Alkyl to Indole Glucosinolates

| PLANT | TOTAL ALKYL GS[1]/GRAM | TOTAL INDOLE GS[2]/GRAM | ALKYL:INDOLE |
|---|---|---|---|
| 5 | 1.06 | 6.33 | 0.17 |
| 6 | 0.69 | 3.52 | 0.20 |
| 7 | 1.09 | 4.19 | 0.26 |
| 8 | 1.21 | 4.64 | 0.26 |
| 9 | 0.95 | 3.33 | 0.29 |
| 10 | 1.12 | 3.85 | 0.29 |
| 11 | 0.89 | 2.93 | 0.30 |
| 12 | 1.51 | 4.76 | 0.32 |
| 13 | 1.49 | 4.70 | 0.32 |
| 14 | 1.90 | 5.92 | 0.32 |
| 1 | 0.31 | 3.12 | 0.10 |
| 15 | 1.67 | 4.45 | 0.37 |
| 16 | 1.26 | 3.25 | 0.39 |
| 17 | 2.57 | 6.04 | 0.43 |
| 18 | 2.60 | 6.05 | 0.43 |
| 19 | 2.34 | 5.32 | 0.44 |
| 20 | 1.47 | 3.03 | 0.49 |
| 21 | 2.26 | 4.64 | 0.49 |
| 22 | 2.32 | 4.73 | 0.49 |
| 23 | 2.79 | 5.59 | 0.50 |
| 24 | 1.35 | 2.70 | 0.50 |
| 25 | 2.38 | 4.74 | 0.50 |
| 26 | 2.75 | 5.11 | 0.54 |
| 27 | 2.53 | 4.65 | 0.55 |
| 28 | 2.58 | 4.34 | 0.59 |
| 29 | 1.90 | 3.11 | 0.61 |
| 30 | 3.80 | 5.92 | 0.64 |
| 31 | 2.71 | 4.13 | 0.66 |
| 32 | 3.11 | 4.55 | 0.68 |
| 33 | 4.37 | 6.16 | 0.71 |
| 34 | 3.86 | 5.31 | 0.73 |
| 35 | 3.41 | 4.51 | 0.76 |
| 36 | 3.92 | 5.15 | 0.76 |
| 37 | 3.03 | 3.90 | 0.78 |
| 38 | 3.65 | 4.46 | 0.82 |
| 39 | 2.69 | 3.21 | 0.84 |
| 40 | 4.66 | 5.49 | 0.85 |
| 41 | 4.15 | 4.82 | 0.86 |
| 42 | 4.57 | 5.24 | 0.87 |
| 1 | 0.31 | 3.12 | 0.10 |
| 43 | 3.05 | 3.45 | 0.88 |
| 44 | 3.41 | 3.80 | 0.90 |
| 45 | 4.60 | 5.06 | 0.91 |
| 46 | 3.98 | 4.33 | 0.92 |
| 47 | 4.60 | 5.01 | 0.92 |
| 48 | 3.71 | 3.85 | 0.96 |
| 49 | 5.19 | 5.19 | 1.00 |
| 50 | 5.56 | 5.29 | 1.05 |
| 51 | 6.39 | 5.89 | 1.09 |
| 52 | 4.94 | 4.54 | 1.09 |
| 53 | 4.56 | 4.07 | 1.12 |
| 54 | 5.47 | 4.77 | 1.15 |
| 55 | 4.94 | 4.26 | 1.16 |
| 56 | 3.96 | 3.26 | 1.21 |
| 57 | 3.67 | 3.02 | 1.21 |
| 58 | 4.35 | 3.41 | 1.27 |
| 59 | 5.61 | 4.16 | 1.35 |
| 60 | 3.64 | 2.60 | 1.40 |
| 61 | 5.43 | 3.86 | 1.40 |
| 62 | 7.59 | 5.40 | 1.41 |
| 63 | 6.94 | 4.84 | 1.43 |
| 64 | 7.96 | 5.55 | 1.43 |
| 65 | 8.42 | 5.81 | 1.45 |
| 66 | 6.95 | 4.73 | 1.47 |
| 67 | 7.21 | 4.74 | 1.52 |
| 68 | 6.53 | 4.10 | 1.59 |
| 69 | 8.59 | 5.17 | 1.66 |
| 70 | 5.99 | 3.54 | 1.69 |
| 1 | 0.31 | 3.12 | 0.10 |
| 71 | 8.74 | 5.15 | 1.70 |
| 72 | 3.01 | 1.61 | 1.87 |
| 73 | 4.80 | 2.55 | 1.89 |
| 74 | 10.40 | 5.33 | 1.95 |
| 75 | 10.04 | 5.12 | 1.96 |
| 76 | 8.84 | 4.42 | 2.00 |
| 77 | 8.03 | 3.86 | 2.08 |
| 78 | 7.54 | 3.59 | 2.10 |
| 79 | 7.13 | 3.37 | 2.12 |
| 80 | 6.62 | 3.02 | 2.19 |
| 81 | 7.25 | 3.09 | 2.34 |
| 82 | 9.27 | 3.93 | 2.36 |
| 83 | 6.63 | 2.78 | 2.38 |
| 84 | 6.91 | 2.80 | 2.46 |
| 85 | 4.94 | 1.96 | 2.52 |
| 86 | 15.24 | 5.94 | 2.56 |
| 87 | 8.19 | 3.04 | 2.70 |
| 88 | 11.83 | 3.33 | 3.55 |
| 89 | 12.86 | 3.07 | 4.19 |
| 90 | 7.61 | 1.51 | 5.03 |
| 91 | 3.59 | 0.56 | 6.42 |
| 92 | 3.72 | 0.31 | 11.84 |
| 93 | 5.87 | 0.41 | 14.20 |
| 94 | 8.22 | 0.56 | 14.65 |
| 95 | 9.13 | 0.47 | 19.60 |
| 96 | 16.99 | 0.72 | 23.59 |
| 97 | 10.87 | 0.39 | 27.88 |

[1]Glucoraphanin + Glucoiberin + Glucoerucin.
[2]Hydroxyglucobrassicin + Glucobrassicin + Neoglucobrassicin.

EXAMPLE 4

Breeding Selected Plants

The individual doubled haploid plants selected as having desirable alkyl/indole glucosinolate ratios are self-pollinated, preferably by bud pollination, as described previously. The progeny seed, or F1 generation, is collected and grown in the field and screened for glucosinolate levels. In this case, the tissue harvested for screening is the market stage broccoli head. Those plants in which the trait is stable are maintained as inbred lines descended from a single plant. The plants are maintained by artificial pollination or by vegetative propagation, as described previously.

The inbred lines may be used directly for the production of market broccoli heads when the lines are agronomically acceptable. Alternatively, the inbred lines may be used for the production of hybrid seed. It is preferable that the other parent used to produce the hybrid seed also be an inbred line expressing high alkyl/indole ratios. Finally, the inbred lines may be used as a source of the trait of enhanced alkyl/indole glucosinolate ratio which may be moved into other broccoli varieties by conventional breeding techniques.

EXAMPLE 5

Use of Plants with High Levels of Chemoprotectants

Plants which exhibit desirable glucosinolate profiles, as evidenced by enhanced alkyl to indole glucosinolate ratios, are used in a variety of ways. Various parts of the plant are consumed as part of the diet. These include market stage heads, seeds, and sprouts. These plant parts are consumed directly if unprocessed, or indirectly if the plant material is processed and used in combination with other foods. Thus, for example, market stage broccoli or cauliflower heads are consumed directly, either cooked or uncooked.

Seeds may be incorporated directly into a food product. The seeds can be used in many different foods such as salads, breads, and other baked goods. Alternatively, the seeds are ground into flour or meal for use as a food or drink supplement. The flour or meal is incorporated into breads, other baked goods, or health drinks or shakes. The flour can be incorporated into pills, capsules or other ingestible formulations.

The seeds are also sprouted to yield sprouts which are also used in a variety of ways. The sprouts can be incorporated immediately into food products such as fresh salads, sandwiches or drinks. The sprouts can be dried and incorporated into pills, capsules or food supplements. Alternatively, non-toxic solvent extracts of the sprouts are made for soups, teas, etc. Typically, sprouts are grown on a non-nutritive solid support, and often in containers which are suitable for shipping and marketing. The sprouts are generally harvested at the two leaf stage (first pair of true leaves) or earlier. Following seed germination, the sprouts are grown from 1 to 20 days, depending upon growth temperature and other abiotic factors, and harvested at the two leaf stage or earlier.

Non-toxic solvent extracts of the seeds or sprouts are useful as healthful infusions or soups. The seeds are extracted with a non-toxic solvent to prepare soups, teas or other drinks and infusions. The sprouts are extracted with cold, warm, or preferably hot or boiling water. If desired, after extraction, the residue of the seeds or sprouts remaining in the extract may be removed. The extract is ingested directly, or it can be further treated. It can, for example, be evaporated to yield a dried extracted product. It can be cooled, frozen, or freeze-dried. It can be mixed with a crucifer vegetable which contains an active myrosinase enzyme. This will accomplish a rapid conversion of the glucosinolates to isothiocyanates, prior to ingestion. Suitable vegetables that contain active myrosinase are of the genus Raphanus, especially daikon, a type of radish.

EXAMPLE 6

Demonstration of High Levels of Glucosinolates and Their Isothiocyanate Congeners in Seed and Sprout Leachates About 600 g of broccoli and of alfalfa seeds were placed in separate, adjacent trays on a commercial-style tray-type sprout cart after disinfection of the seeds by immersing them in a solution of 25% of a commercial bleach preparation (such as Clorox) in water for 15 minutes, and then exhaustively rinsing the seeds with water, according to commonly accepted protocols used by the sprouting industry. The seeds were then placed in an inclined sprouting tray, rinsed again with spray from an overhead mist nozzle, then allowed to sit undisturbed for 1 hour, following which water was delivered via overhead mist until about 200 ml of liquid per sprouting tray had run off and been collected. Misting was continued using six 20-second sprays per hour until the next collection period, at which time the trays were again left undisturbed for 1 hour, then the leachate was rinsed away with fresh water and collected. The leachates, which were straw-colored at pH 6.8, were analyzed for the amounts and types of glucosinolates present.

The levels of isothiocyanate in the waste/rinse waters, collectively termed "the leachate," from broccoli seeds and sprouts increased from about 13 $\mu$M after the first hour of growth following the seed disinfection treatment, to about 192 $\mu$M after the seventh hour of growth. Levels of glucoraphanin (the precursor of sulforaphane) reached about 0.33 mM by the seventh hour, and glucosinolates recovered consisted of 99.4% glucoraphanin and 0.6% neoglucobrassicin. In contrast, there were no traces of these compounds from alfalfa seeds/sprouts treated in the same manner.

Recovery of total dissolved solids (dry weight) from the hourly broccoli leachate collections ranged from 3.9 to 5.2 mg/ml. Total recovery of glucoraphanin from the seeds was as high as 81.5 nmol/g seed/h. If leaching is continued for one-half day, it contains about 1 nmol of glucoraphanin or about 20% of the total glucoraphanin content of the seed used in these experiments.

EXAMPLE 7

Growth Inhibitory Effect of Broccoli Seed and Sprout Leachate on Bacterial Growth Leachate prepared as described in Example 6 had a potent inhibitory effect on the growth in broth culture of *E. coli* strain DH10B. This effect was observed in multiple experiments performed on leachate collected from multiple sprout preparations.

1. Effect of Leachate from Germinated Broccoli and Alfalfa Seeds/sprouts on Bacterial Growth in Normal and Low Nutrient Medium Bacterial growth was monitored in complete Luria Broth ("1xLB", a standard medium for cultivating such microbes), as well as in low nutrient medium, or 0.1xLB. The culture medium were prepared by adding the dry ingredients (10 g/L tryptone, 5 g/L yeast extract, and 10 g/L NaCl for full-strength medium) to the appropriate volume of leachate from collections made following disinfection of the seeds as described in Example 6. Once the dry 1x or 0.1xLB ingredients were solubilized, the pH was adjusted to pH 7.5 with NaOH, and the medium was filter-sterilized and used for the cultivation of *E. coli*.

Figure 1:
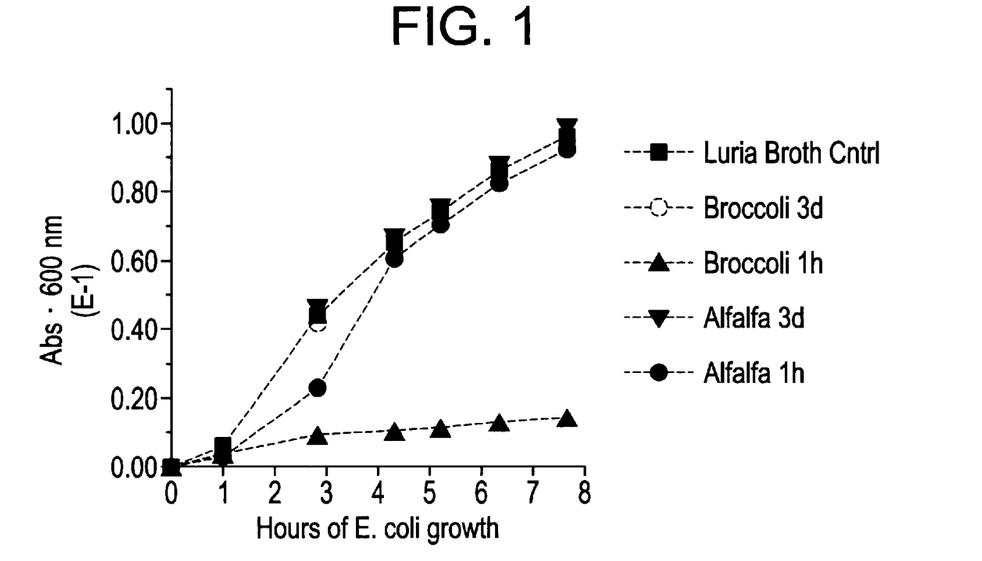
FIG. 1 shows the effect of broccoli and alfalfa sprout leachate on the growth of *E. coli* in 0.1×Luria Broth.

There was a substantial inhibitory effect of broccoli sprout leachate. Surprisingly, this effect was even more dramatic in a low nutrient medium background (0.1xLB), which is in fact more representative of the actual "nutrient conditions" existing during the sprouting process (FIG. 1). In contrast, no inhibitory effect of the leachate obtained from alfalfa sprouts was observed. Although initial tests indicate that this growth inhibitory activity of broccoli sprout leachate is stable to freeze-drying and to heating to 50° C., the activity appears to be rapidly lost upon mixing with an agar base.

2. Effect of Leachate Obtained at Different Times During Germination from Broccoli Seeds/sprouts on Bacterial Growth Leachates were prepared as described in Example 6, and *E. coli* growth in 0.1xLB made as described in Example 7.1. was monitored. The 0.1xLB was prepared with leachates collected after the first, fourth, and seventh hour of broccoli seed germination.

Figure 2:
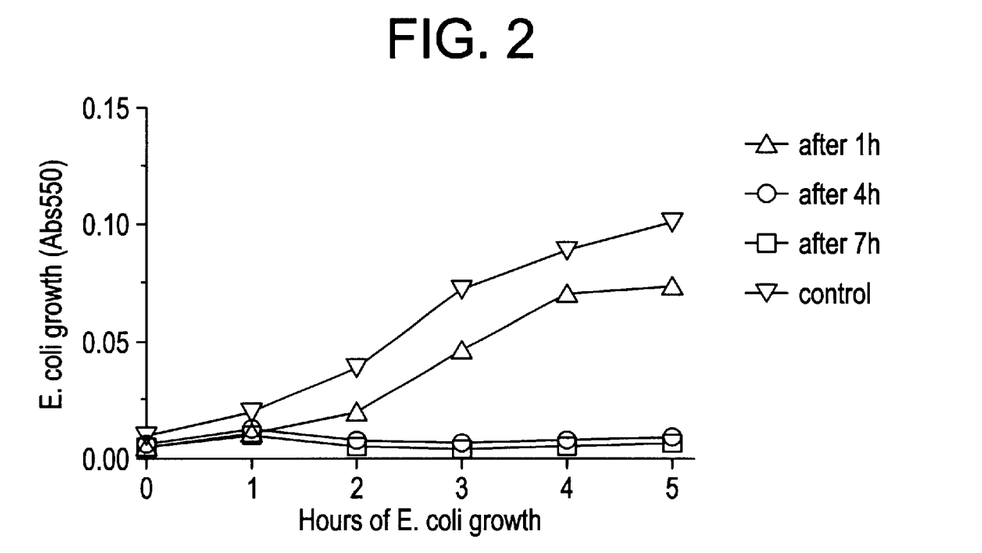
FIG. 2 shows the effect of broccoli sprout leachate collected at different times during germination on the growth of *E. coli*.
Figure 3:
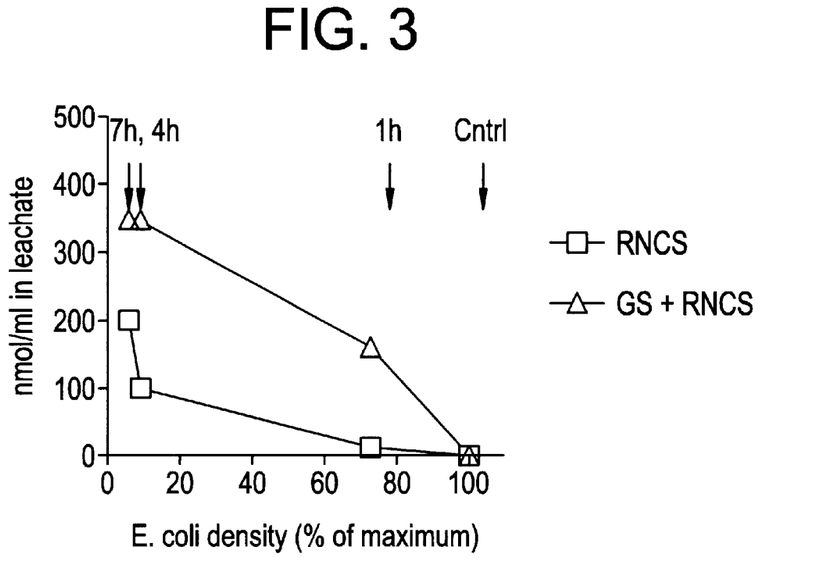
FIG. 3 shows the effect of glucosinolate and isothiocyanate concentration in the leachate collected from broccoli sprouts on the growth of *E. coli* in 0.1×Luria Broth.
Figure 4:
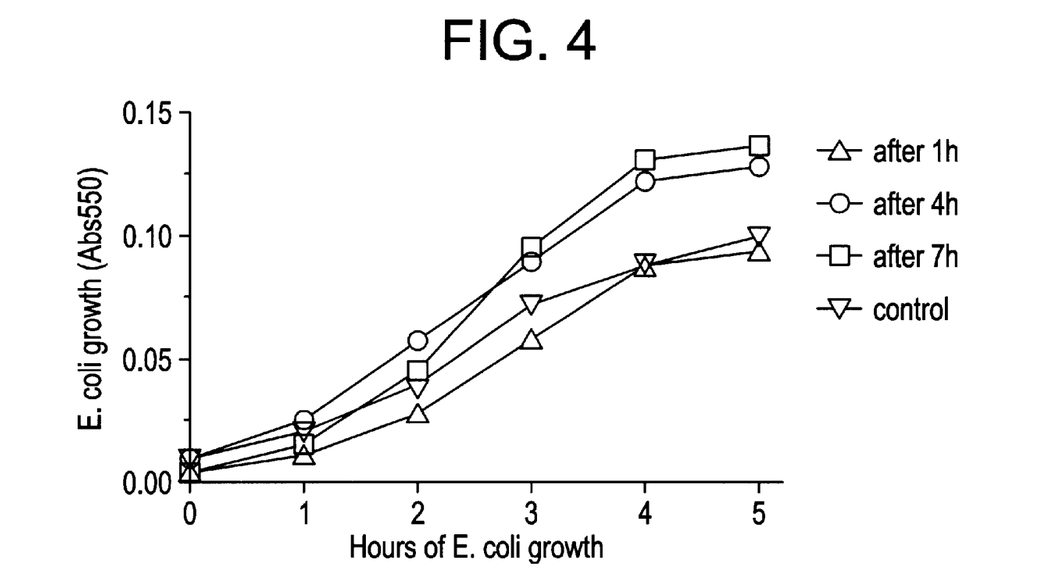
FIG. 4 shows the effect of alfalfa sprout leachate collected at different times during germination on the growth of *E. coli*.

There was a potent inhibitory effect of the broccoli seed/sprout leachate on bacterial growth which increased with time over germination (FIG. 2). The differential effects were rank-correlated with the isothiocyanate content and with the glucosinolate-isothiocyanate content of the leachate (FIG. 3), and the effect had disappeared by the third day of broccoli sprout growth. As in Example 6, there was a stimulatory effect of alfalfa seed leachates on bacterial growth (a 34% increase in final bacterial titer was observed with the 7 h leachate). None of the alfalfa sprout leachates showed any growth inhibitory effect on the bacteria (FIG. 4).

3. Effect of Leachate Obtained from 4- and 7-hour Germinated Broccoli Seeds/sprouts (pooled) on Staphylococcus sp. Growth Growth of *Staphylococcus aureus* and an unidentified Staphylococcus sp. was inhibited by a 50% and a 25% dilution of the leachate from 4- and 7-hour germinated broccoli seeds/sprouts (pooled) collected as described in Example 6. These tests were conducted in a semi-solid (agar) matrix, using a Tripticase Soy, high protein growth medium, and a standard Minimum Inhibitory Concentration assay system. Since antibiotic activity appears to be rapidly lost in an agar-based test system, these results probably represent the low end of the range of possible growth inhibitory effects of these compounds.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims. All publications and patent applications mentioned in this specification are indicative of the level of skill of those in the art to which the invention pertains.

All publications and patent applications are herein incorporated by reference to the same extent as if each individual publication or patent application were specifically and individually indicated to be incorporated by reference in its entirety.

I claim:

1. A method for selecting a cruciferous plant comprising:
   (a) providing a plant,
   (b) measuring the ratio of alkyl glucosinolate to indole glucosinolate in a tissue of said plant, and
   (c) selecting the plant if the ratio is greater than 6.
2. The method of claim 1, wherein the plant is a double haploid plant.
3. The method of claim 2, wherein the double haploid plant is obtained by an anther culture technique.
4. The method of claim 1, wherein the plant is a mutagenized plant.
5. The method of claim 4, wherein the plant was mutagenized with a chemical mutagen before (a).
6. The method of claim 5, wherein the chemical mutagen is ethylmethane sulfonate.
7. The method of claim 1, wherein the plant is a broccoli plant.
8. The method of claim 7, wherein the plant belongs to a cultivar selected from the group consisting of Saga, DeCicco, Everest, Emerald City, Packman, Corvet, Dandy Early, Emperor, Mariner, Green Comet, Green Valiant, Arcadia, Calabrese Caravel, Chancellor, Citation, Cruiser, Early Purple Sprouting Red Arrow, Eureka, Excelsior, Galleon, Ginga, Goliath, Green Duke, Greenbelt, Italian Sprouting, HiSierra, Late Purple Sprouting, Late Winter Sprouting White Star, Legend, Leprechaun, Marathon, Mariner, Minaret (Romanesco), Paragon, Patriot, Premium Crop, Rapine (Spring Raab), Rosalind, Salade (Fall Raab), Samurai, Shogun, Sprinter, Sultan, Taiko, and Trixie, and Viking.
9. The method of claim 7, wherein the plant belongs to a cultivar selected from the group consisting of Viking, Everest, HiSierra, and Marathon.
10. The method of claim 1, wherein the plant is a cauliflower plant.
11. The method of claim 10, wherein the plant belongs to a cultivar selected from the group consisting of Alverda, Amazing, Andes, Burgundy Queen, Candid Charm, Cashmere, Christmas White, Dominant, Elby, Extra Early Snowball, Fremont, Incline, Milkyway Minuteman, Rushmore, S-207, Serrano, Sierra Nevada, Siria, Snow Crown, Snow Flake, Snow Grace, Snowbred, Solide, Taipan, Violet Queen, White Baron, White Bishop, White Contessa, White Corona, White Dove, White Flash, White Fox, White Knight, White Light, White Queen, White Rock, White Sails, White Summer, White Top, and Yukon.
12. A method for producing a progeny cruciferous plant comprising:
   (a) measuring the ratio of alkyl glucosinolate to indole glucosinolate in a tissue of a potential parent plant,
   (b) selecting the potential parent plant if the ratio is greater than 6, and
   (c) producing a progeny plant from the selected plant.
13. The method of claim 12,
   wherein the ratio of alkyl glucosinolate to indole glucosinolate in a tissue of the progeny plant is higher than the ratio of alkyl glucosinolate to indole glucosinolate in a tissue of the selected plant, and
   wherein the tissue of the progeny plant and the tissue of the selected plant is of the same type.

* * * * *